(12) United States Patent
Lei et al.

(10) Patent No.: US 9,538,909 B2
(45) Date of Patent: Jan. 10, 2017

(54) SELF-ILLUMINATING CMOS IMAGING PACKAGE

(71) Applicant: OmniVision Technologies, Inc., Santa Clara, CA (US)

(72) Inventors: Junzhao Lei, San Jose, CA (US); Guannho G. Tsau, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 239 days.

(21) Appl. No.: 13/936,844

(22) Filed: Jul. 8, 2013

(65) Prior Publication Data

US 2015/0018611 A1    Jan. 15, 2015

(51) Int. Cl.
| | |
|---|---|
| *H01L 27/15* | (2006.01) |
| *A61B 1/06* | (2006.01) |
| *A61B 1/05* | (2006.01) |
| *H01L 31/173* | (2006.01) |
| *H01L 25/16* | (2006.01) |

(52) U.S. Cl.
CPC ............ *A61B 1/0676* (2013.01); *A61B 1/051* (2013.01); *A61B 1/0684* (2013.01); *H01L 27/15* (2013.01); *H01L 31/173* (2013.01); *H01L 25/167* (2013.01); *H01L 2224/48247* (2013.01); *H01L 2924/181* (2013.01)

(58) Field of Classification Search
CPC .................... H01L 2924/00; H01L 2924/0002
USPC .............................................. 257/82, 80, 81
See application file for complete search history.

(56) References Cited

U.S. PATENT DOCUMENTS

| | | | |
|---|---|---|---|
| 6,449,006 B1* | 9/2002 | Shipp .............................. 348/70 |
| 6,583,445 B1* | 6/2003 | Reedy et al. .................... 257/82 |
| 2007/0055105 A1* | 3/2007 | Matsuzawa ........ A61B 1/00096 600/176 |
| 2009/0003857 A1* | 1/2009 | Kuramochi et al. ............ 399/45 |
| 2012/0006971 A1* | 1/2012 | Pflibsen et al. ............ 250/208.1 |

FOREIGN PATENT DOCUMENTS

JP         2012070232      *   4/2012

OTHER PUBLICATIONS

Taiwanese Patent Application 103121089 Office Action Jun. 18, 2015 with Concise Explanation 14 pages.
Taiwanese Patent Application 103121089 Office Action dated Jan. 4, 2016, 11 pages.

* cited by examiner

*Primary Examiner* — Samuel Gebremariam
(74) *Attorney, Agent, or Firm* — Lathrop & Gage LLP

(57) ABSTRACT

A microelectronics chip contains an integrated CMOS imaging sensor integrated with a LED die. Circuitry is established on the chip for a shared power arrangement.

19 Claims, 8 Drawing Sheets

US 9,538,909 B2

SELF-ILLUMINATING CMOS IMAGING PACKAGE

BACKGROUND OF THE INVENTION

Complementary metal oxide semiconductor (CMOS) image sensor products have many uses, for example, in cameras, smart phones, and medical imagers. All such devices require external light. This is particularly evident in medical endoscope products. The endoscope tip needs a light source because it is dark inside the body. Second, the endoscope tip needs to be miniaturized due to the medical necessity to access small cavities inside the body, such as tributaries of airway or blood vessels. As a result, the requirement for supplemental illumination may sometimes impose a limiting factor on further miniaturization of endoscopes, especially as the requirement complicates the design by requiring a power delivery system for the illumination source.

Conventional endoscope products have separate systems of illumination and detection. These are shown by way of example in U.S. Pat. No. 6,449,006 issued to Shipp, and related optical assembles may be seen in U.S. Pat. No. 8,308,637 issued to Ishigami et al. FIG. 1 shows generally an endoscope system 100 of this nature in the prior art. An endoscope 102 is provided with an imaging tip 104 that is selectively attachable at locking collar 106. A CMOS imaging package 108 includes a lens and a photodectector array, such as an array of photodiodes (not shown). The imaging package 108 is circumscribed by a plurality of light emitting diodes (LEDs) 110, 112. Wiring harness 114 couples the imaging tip 104 with a host controller 116 by use of individual leads allocated to the LEDs 110, 112 and the CMOS imaging package 108 for the receipt of signals that are processed to develop viewable images.

SUMMARY OF THE INVENTION

The presently disclosed instrumentalities overcome the problems outlined above and advance the art by providing a CMOS imaging package that incorporates one or more LEDs as may be needed to provide illumination for imaging purposes.

In one embodiment, a microelectronics chip bearing a CMOS imaging sensor is improved by integrating the LED emitter with the chip, such that the LED emitter and the ship share a common substrate. By way of example, this integrated device may be formed as a chip package and used in an endoscope, camera, or other imaging device that may benefit from illumination from time to time.

In one aspect, the substrate may be made of silicon, but GaAs is preferred. The LED portion of the microelectronics chip may be formed over AlGaAs. In this example the CMOS sensor portion may be formed over InGaAs. The microelectronics chip may contain other circuitry facilitating operation of the microelectronics chip, and this circuitry may be formed over unmodified GaAs.

In one aspect, the microelectronics chip may include a LED lens compartment providing a first optical pathway for projecting light from the LED emitter. A CMOS sensor lens compartment may also be provided to furnish a second optical pathway that delivers light to the CMOS imaging sensor. An optical divider may be placed between the LED lens compartment and the CMOS sensor lens compartment to substantially isolate the first optical pathway from the second optical pathway.

In one aspect, the LED emitter and the CMOS imaging sensor share power through at least one common electrical connection on the microelectronics chip. This electrical connection may be, for example, a shared power lead and/or a shared ground lead.

The CMOS sensor on the microelectronics chip may be configured in either a FSI or BSI orientation.

DETAILED DESCRIPTION OF THE DRAWINGS

An illumination source may be incorporated into a CMOS imaging package according to the various embodiments shown below.

CMOS Sensor and Optical Diode with Shared Electrical Connection

An optical diode, such as a LED, may be formed into a die that is inserted into the peripheral structure of a CMOS sensor package. More specifically, the LED utilizes existing electrical leads of the CMOS sensor package. Typical CMOS packages use 30 to 50 mW of power, but LEDs may use 100 to 500 mW power, so this need may be easily accommodated in the design of CMOS power lines for this use. Also, LEDs may come with or without lenses. The LED may need a lens to project light outward if a lighting range of 50 mm is required. If the lighting range is less than 50 mm, then the LED may not need a lens to project light outward.

Figure 1:
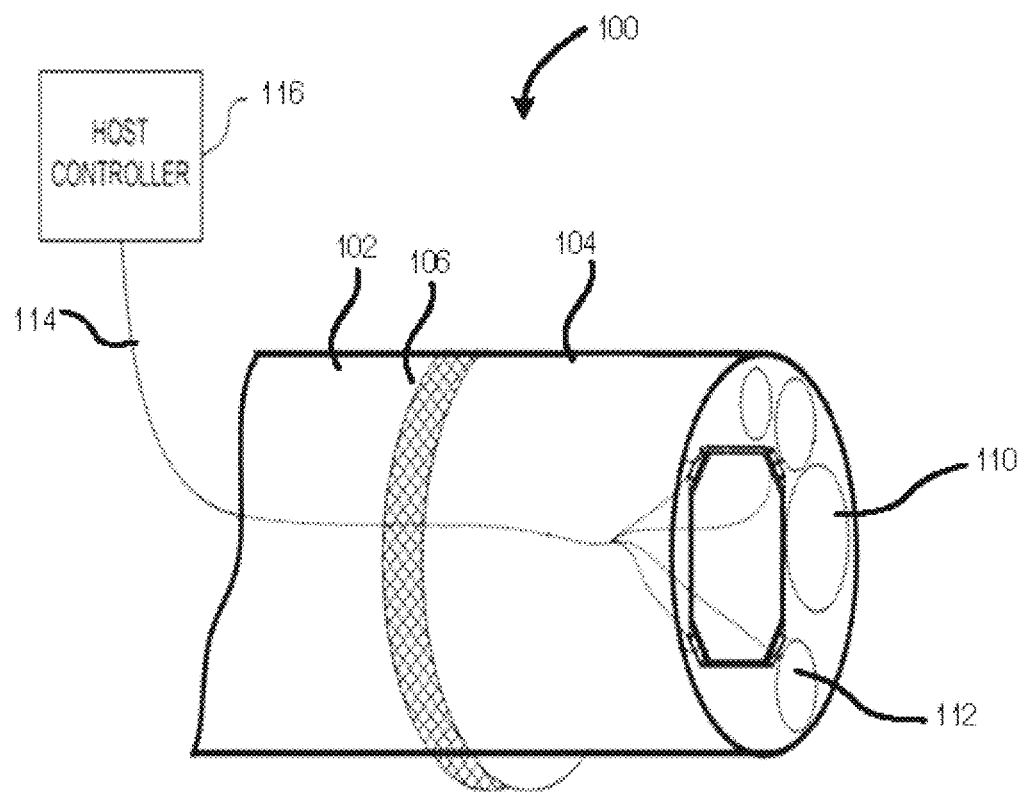
FIG. 1. shows an illuminated endoscope tip according to the prior art.
Figure 2:
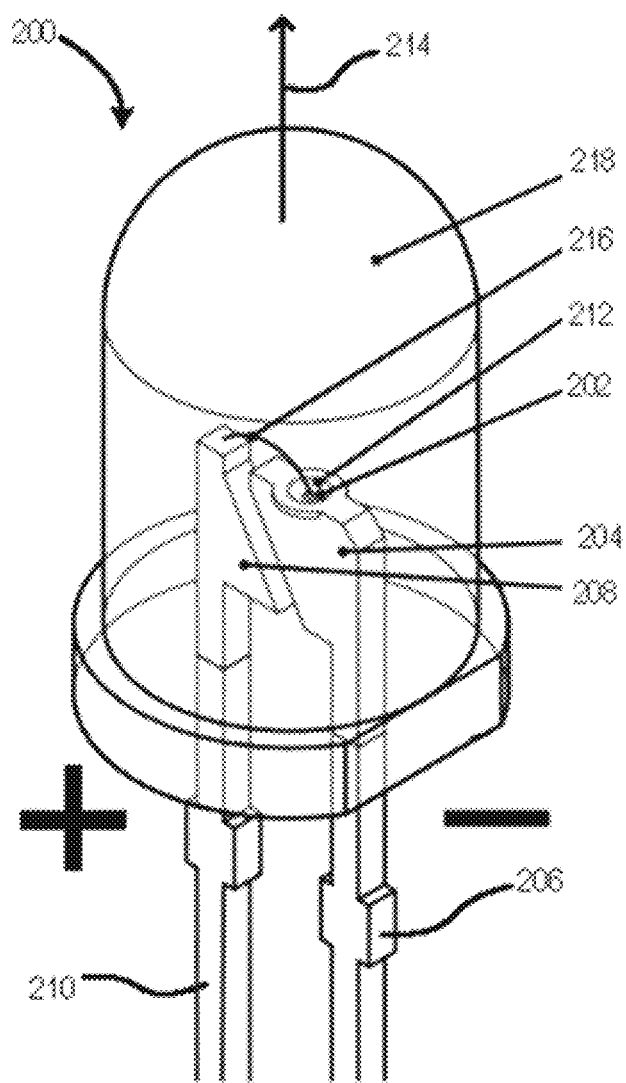
FIG. 2 shows a light emitting diode (LED)

FIG. 2 shows a basic structure for a conventional LED 200. The light-emitting semiconductor LED die 202 is the heart of the LED, but it is a very small part of the LED. The LED die 202 is surrounded by bulky support structures, including an anvil 204 that is connected to a cathode 206, a post 208 that is connected to an anode 210, a reflective cavity 212 that surrounds the die 202 and concentrates light in a forward direction 214, a wire bond 216, and a lens 218, such as an epoxy lens case. It will be appreciated in context of the embodiments discussed below that the LED die 202 is singled out and incorporated with the CMOS sensor by sharing power and/or ground leads. There is no need for the additional bulky LED components including the anvil 204 and post 208 as shown in FIG. 2

Figure 3:
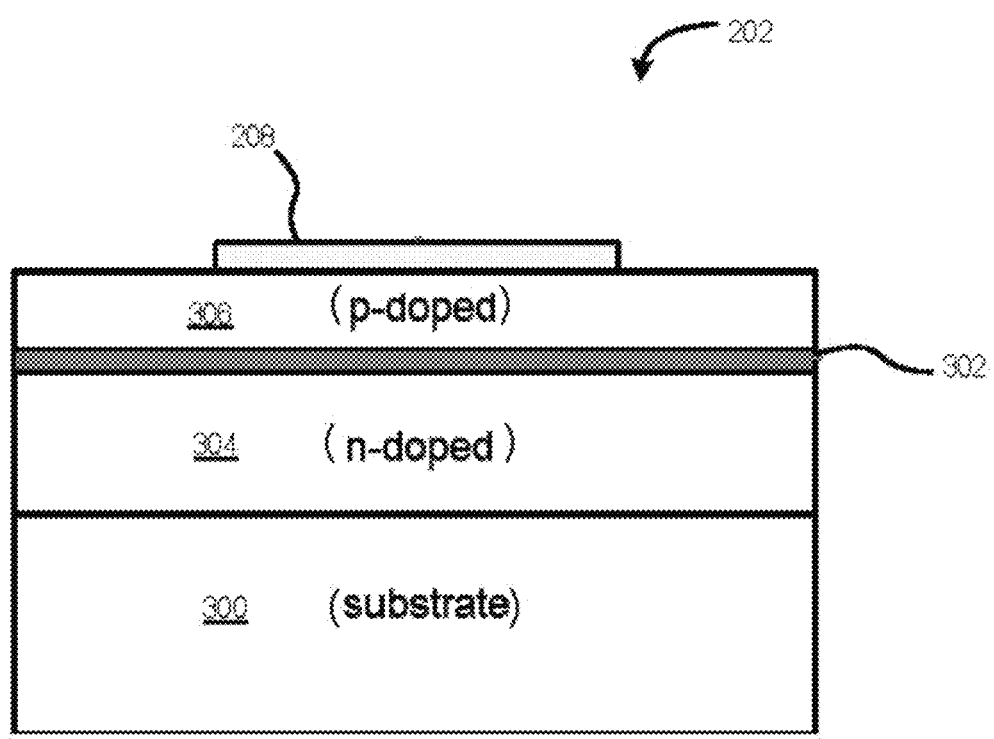
FIG. 3 shows a LED die that may be adapted for use as described herein.

FIG. 3 is a midsectional view of the LED die 202. The LED die 202 is formed on a substrate 300 including Group III and/or V elements, such as GaAsP or AlGaInP. Noticeably, the LED substrate may be made of substances other than Si, which is conventionally used to form CMOS sensor. The light producing portion is the active epitaxy layer 302, which is sandwiched between a n-doped layer 304 and a p-doped layer 306. Electrical connection to the p-doped layer is made through a p-contact 308 at the top of the LED die 202.

Figure 4:
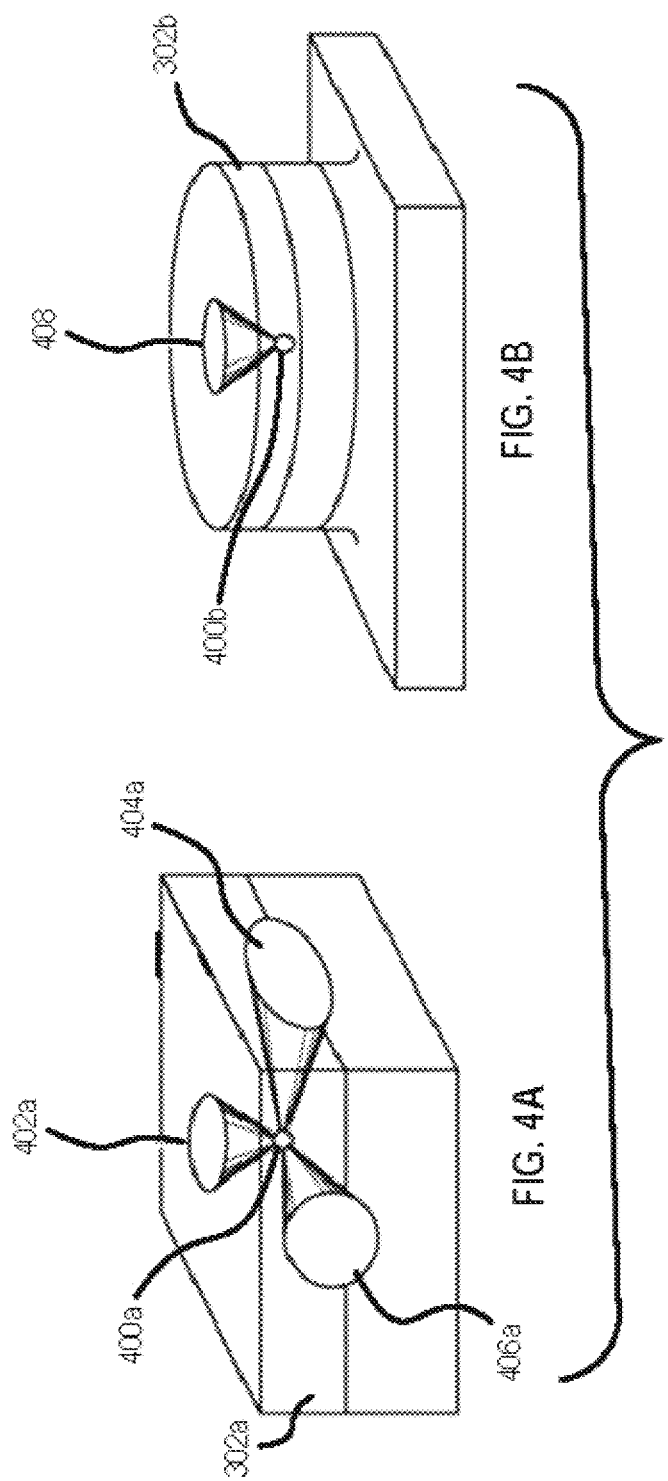
FIG. 4A shows light emanating from a LED die in a plurality of directions and FIG. 4B shows a comparable structure with light that is directionally restricted by provision of a reflecting surface.

Generally speaking, active epitaxial layer 302 emits light in two directions—upwards and sideways. FIG. 4A shows light from a point source 400a in a rectangular epitaxial layer 302a being emitted both upwards 402a and sideways 404a, 406a. FIG. 4B shows light from a point source 400b in a cylindrical epitaxial layer 302b being emitted only upwards 402b by operation of a conical reflective cavity 408.

Figure 5:
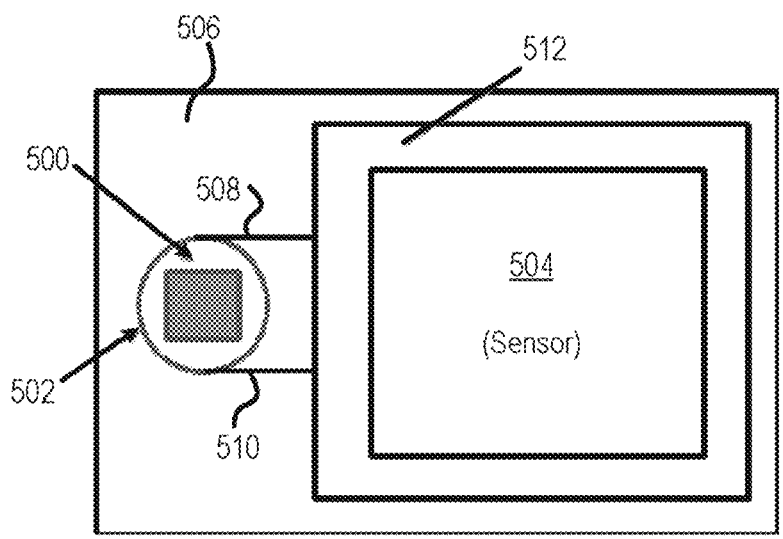
FIG. 5 shows a CMOS imaging sensor that is integrated with a LED die with shared substrate and power leads.

A first embodiment of shared electrical connection is shown in FIG. 5. Here, a LED die 500 and its associated reflective surface 502 are incorporated with CMOS sensor 504 at the sensor's carrier 506. Electrical leads, e.g., power 508 and ground 510, are situated on the carrier 506. The LED die 500 shares these electrical leads with CMOS sensor 504, for example, in a shared power coupling arrangement at the periphery 512 of the sensor 504. While FIG. 5 shows only one LED die 500 associated with the CMOS sensor 504, there may be a number of LEDs associated with a single sensor. The CMOS sensor 504 may either be front side illuminated (FSI), where metal layers are on top of photodiode, or back side illuminated (BSI) where metal layers and photodiodes are on opposite sides. Both of the FSI and BSI sensor configurations will work because the electrical leads are situated at the carrier level.

Figure 6:
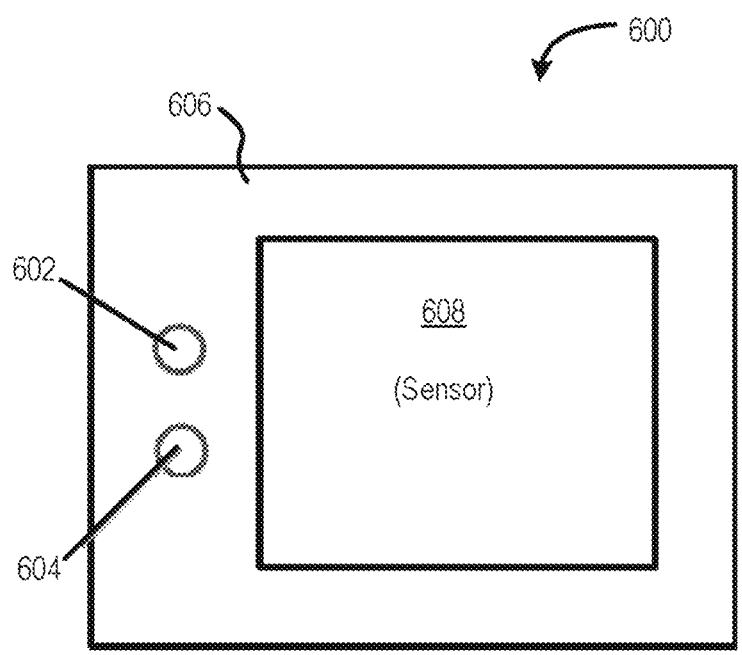
FIG. 6 is a device like that of FIG. 5, but with a different arrangement for sharing of power.

In a second embodiment, the LED die and its associated reflective surface are incorporated at the periphery of the CMOS sensor chip. FIG. 6 shows a CMOS sensor array 600, such as one having dimensions of 0.9 mm×0.9 mm, with a power lead 602 and a ground lead 604, e.g., 0.25 mm×0.25 mm, in the periphery around the pixel array or CMOS sensor 608. The LED die (not shown) may be situated on top of power and ground leads 602, 604, and may share power and ground with the CMOS sensor 608. In this embodiment, the CMOS sensor 608 must be FSI, because the electrical leads on the periphery 606 are accessible at the same side as the pixel array or CMOS sensor 608 that includes photodiodes.

Lensing Camera Chip Incorporated with LED

The foregoing embodiments of FIGS. 5 and 6 may be improved by adding a single divided optical lens for both light projection from the LED die and light collection for the CMOS sensor. This concept applies semiconductor stacking methodology to fabricate wafer level optical elements as layers of wafer structure. It incorporates the optical wafer structures into the packaging of CMOS sensors in a single step. This results in a fully integrated chip product, capable of achieving camera functionality on reflowable CMOS silicon chips with very small footprints and low profiles to produce ultra-thin and compact devices.

Figure 7:
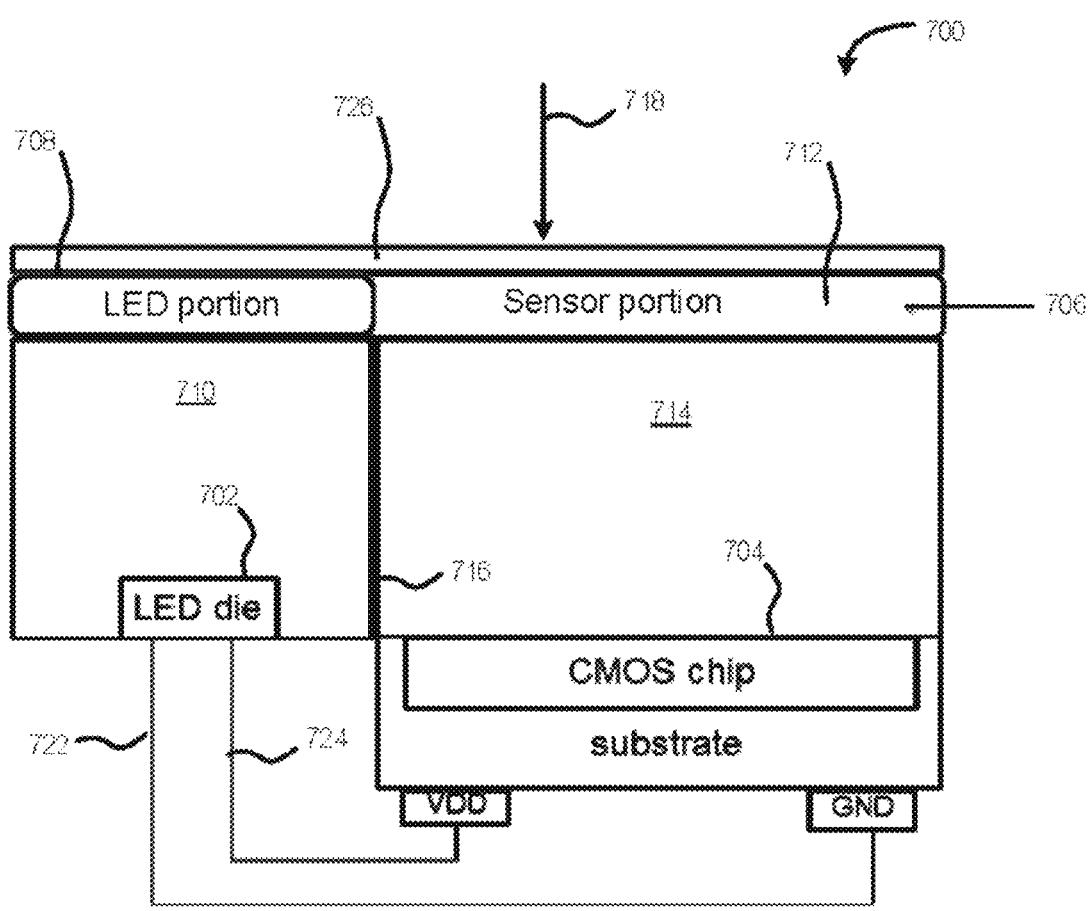
FIG. 7 shows a chip package with a CMOS sensor and a LED die built onto a shared substrate with common leads for the sharing of power on the substrate, where also the package includes a lens covering both the LED die and the CMOS sensor.

FIG. 7 shows one such embodiment as a cube chip 700. A LED die 702 and CMOS chip 704 share a common lens 706 including a LED lens portion 708 atop a LED lens compartment 710 and a sensor lens portion 712 atop a sensor compartment 714. An optical divider 716 separates the LED lens compartment 710 from the sensor compartment 714. The optical divider is made of, or is coated with, an opaque material to prevent light produced by the LED die 702 from straying into the sensor compartment 714. The sensor lens portion 712 concentrates incoming light 718 for projection onto the CMOS sensor 704. This generally means that the sensor lens portion 712 of the lens is convex, i.e., positive.

The LED lens portion 708 channels light 720 emitting from the LED die 702 out of the LED compartment 708. LED lens portion 708 may be convex or positive for the purpose of converging light, or else it may alternatively be concave or negative for the purpose of diverging light. The optic characteristics of the LED lens portion and the sensor lens portion may be different due to light convergence/divergence. In the case where both portions 708, 712 are light-converging, they may have different focal depths. Leads 722, 724 share power between the CMOS chip 704 and the LED die 702, such as by sharing power from the VDD rail and ground, as is also disclosed above. An optional top layer 726 of relatively increased hardness, such as cover glass, may protect the common lens 706.

The common lens 706 may be stamped or embossed from one piece of epoxy, for example, where a press used to shape common lens 706 includes a first part complementary to the LED lens portion 708 for the forming of that portion and a second part complementary to the sensor lens portion 712. When the common lens 706 is made alternatively with photolithography techniques, the photo mask covers both the LED section and the sensor section.

Figure 8:
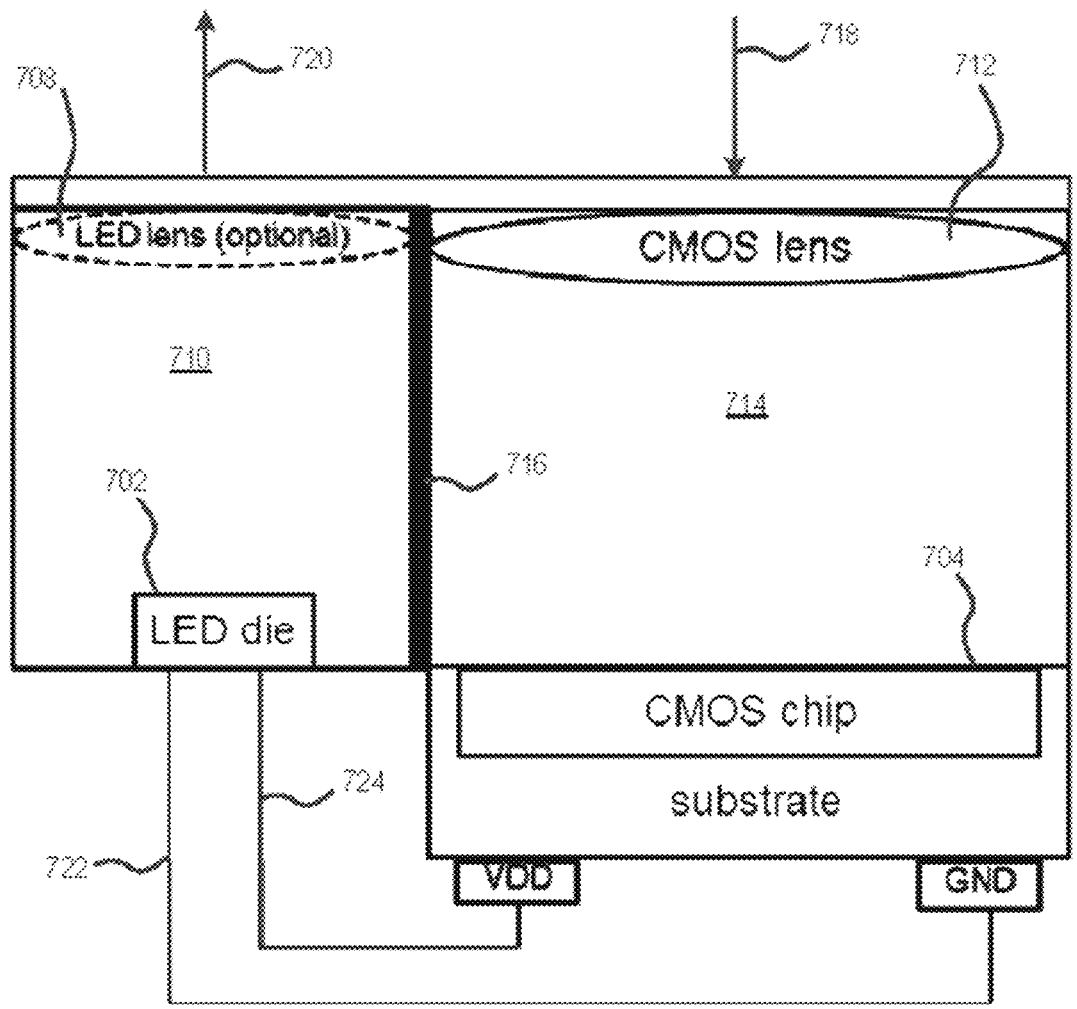
FIG. 8 shows a chip package with a CMOS sensor and a LED die built onto a shared substrate with common leads for the sharing of power on the substrate, where also the package includes a lens covering at least one of the LED die and the CMOS sensor.

FIG. 8 shows an embodiment like that of FIG. 7, but wherein the common lens 706 only covers the sensor compartment 714. Like numbering of identical parts is retained between FIGS. 7 and 8 to show that the LED lens portion 708 is optionally omitted.

Manufacture of LED and CMOS Sharing One Substrate

The basic idea is to make CMOS and LED on the same substrate such as GaAs. CMOS is conventionally made on Si substrate. However, GaAs may also be used as an alternative substrate for CMOS devices. LED is generally made on AlGaAs substrate, which may be formed from GaAs. Therefore, it is possible to start off with GaAs, modify the CMOS portion and LED portion accordingly, and then proceed to make LED and CMOS devices on the modified portions of the substrate.

GaAs has a lattice constant of 565.35 pm. AlGaAs has a lattice constant of 565.33 pm, so it may be formed by growing the crystalline lattice onto a GaAs substrate without causing any significant lattice strain. In contrast, InGaAs has a lattice constant of 586.87 pm, so it may not be formed onto a GaAs substrate without causing significant lattice strain. In fact, the conventional method of forming InGaAs is to grow the crystalline lattice onto InP. In the present disclosure, InGaAs is formed by implanting Indium into a GaAs substrate. AlGaAs may be formed by either growing it on GaAs substrate, or by implanting Al into GaAs.

On the LED side, modification into AlGaAs by implanting Al produces an infrared (IR) emitter that generates IR light having a wavelength of greater than about 760 nm. Conversely, modification of the sensor side into InGaAs by implanting In yields a detector capable of detecting IR in the spectral range of 700-2600 nm.

Figure 9:
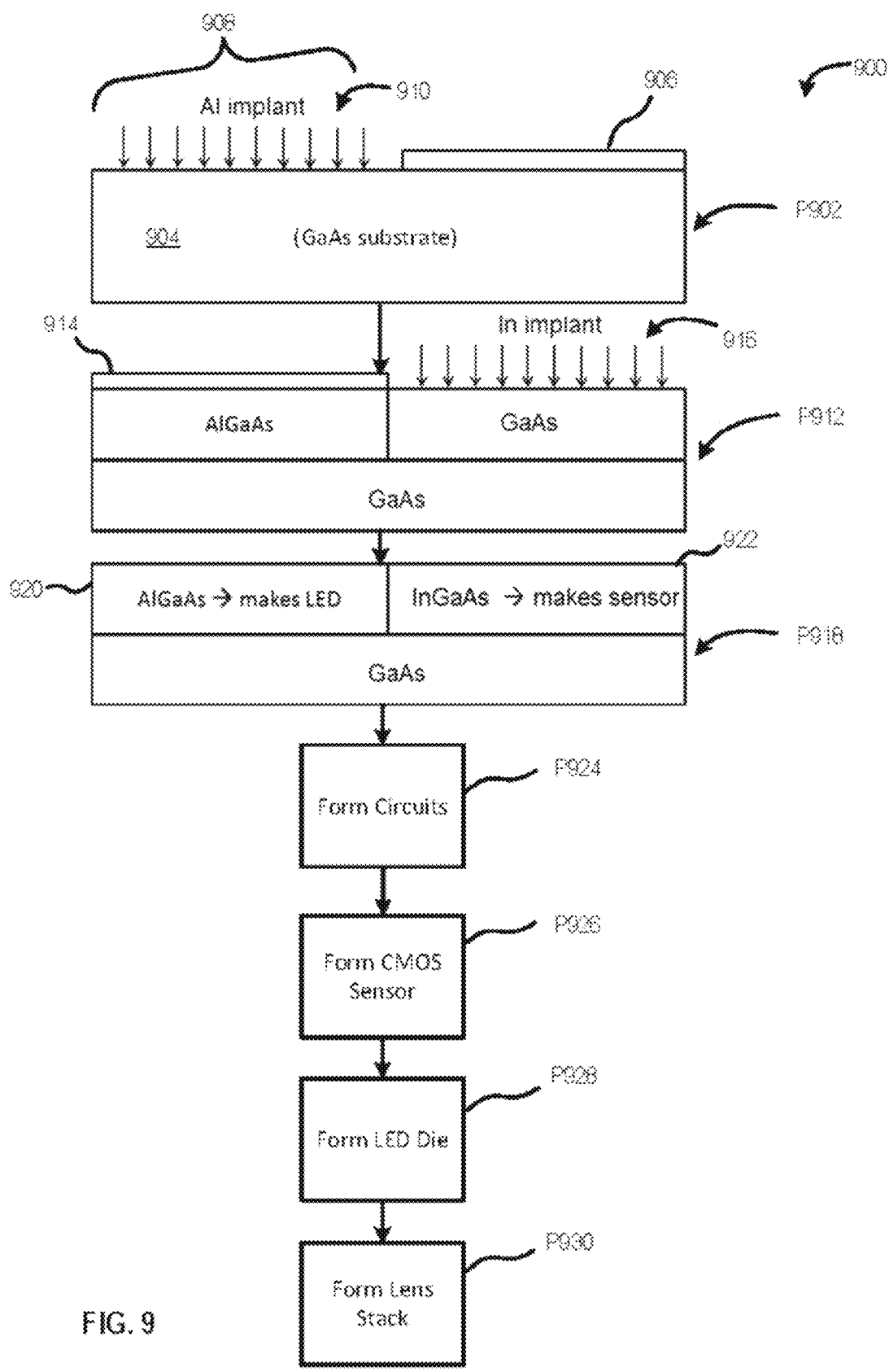
FIG. 9 is a process diagram for the manufacture of chip packages that include both a LED die and a CMOS sensor.

FIG. 9 shows, by way of example, a process for making an integrated substrate as described above. The substrate may include a AlGaAs portion for LED and a InGaAs portion for CMOS image sensor. The process 900 starts in step P902 with covering a GaAs substrate 904 with a photoresist 906 that is removed in area 908 for aluminum implantation 910 to form AlGaAs. Step P912 entails removing the photoresist 906 with the addition of a new photoresist 914 to cover the AlGaAs material in region 908. Indium is now implanted 916 into the exposed GaAs portion that formerly underlay photoresist 906 to form InGaAs. Finally, the photoresist 914 covering the AlGaAs portion is removed P918. The resulting substrate has an AlGaAs portion for LED use, and an InGaAs portion 922 for the CMOS image sensor.

Other electrical circuits that are necessary for the image sensor function, e.g., supporting components including logic circuits such as read out circuits, may be formed P924 on the GaAs substrate that has not been implanted with Al or In.

The CMOS sensor is formed P926 on the InGaAs material 922 resulting from step P918. Details of manufacturing the CMOS sensor are known to the art, for example, as described in U.S. Pat. No. 5,631,704 issued to Dickinson et al., and U.S. Pat. No. 6,133,563 issued to Clark et al., both of which are incorporated by reference to the same extent as though fully replicated herein. The LED die is formed P928 on the AlGaAs material 920 resulting from step P912. Details of manufacturing the LED die are known to the art, for example, as described in U.S. Pat. No. 5,032,960 issued to Katoh et al., and U.S. Pat. No. 8,368,114 issued to Yang, both of which are incorporated by reference to the same extent as though fully replicated herein.

In step P930, a combined lens is formed for use with both the LED die and the CMOS sensor. This lens may be formed, for example, utilizing a process such as stamping or embossing. A portion of the lens is for LED projection and the other portion is for CMOS light receiving, as described above. This lens set is stacked onto the integrated LED-CMOS chip. The final product is an integrated system made of a chip set and a lens set that can emit light by action of the LED die, as well as detect light by action of the CMOS image sensor. Further, when multiple CMOS image sensors are integrated into this system, these multiple sensors may be used for 3D imaging.

Those skilled in the art will appreciate that the foregoing discussion teaches by way of example and not by way of limitation. What is shown and described may be subjected to insubstantial change without departing from the scope and spirit of the invention. Accordingly, the inventors hereby announce their intention to rely upon the Doctrine of Equivalents, if needed in order to protect their full rights in what is claimed.

What is claimed is:

1. In a microelectronics chip bearing a complementary metal oxide semiconductor (CMOS) image sensor, the improvement comprising:
 a Gallium-Arsenide (GaAs)-based substrate including (i) a first portion that is a component of the CMOS image sensor, and (ii) a second portion that is a component of a light emitting diode (LED), at least one of (a) the first portion being implanted with a first element and (b) the second portion being implanted with a second element different from the first element.

2. The microelectronics chip of claim 1, the first portion being implanted with the first element, the second portion being implanted with the second element.

3. The microelectronics chip of claim 2, the first element being indium (In), the first portion being InGaAs.

4. The microelectronics chip of claim 2, the second element being aluminum (Al), the second portion being AlGaAs.

5. The microelectronics chip of claim 2, the first element being indium (In), the first portion being InGaAs, the second element being aluminum (Al), the second portion being AlGaAs.

6. The microelectronics chip of claim 2, the improvement further comprising circuitry configured for facilitating operation of the microelectronics chip, the circuitry being formed over an unmodified GaAs portion of the GaAs-based substrate.

7. The microelectronics chip of claim 1, the improvement further comprising: at least one common electrical connection disposed on the substrate and shared by the LED and the CMOS image sensor.

8. The microelectronics chip of claim 7, the at least one common electrical connection including a power lead.

9. The microelectronics chip of claim 7, the at least one common electrical connection including a ground lead.

10. The microelectronics chip of claim 7, the least one common electrical connection including a power lead and a ground lead.

11. The microelectronics chip of claim 10, the CMOS image sensor located on the substrate in a front side illuminated orientation.

12. The microelectronics chip of claim 10, the CMOS image sensor located on the substrate in a back side illuminated orientation.

13. The microelectronics chip of claim 1, further comprising:
 a monolithic optical lens optically coupled with the LED and the CMOS image sensor.

14. The microelectronics chip of claim 13, the single monolithic optical lens comprising:
 a first lens portion for projecting light emitted by the LED; and
 a second lens portion for collecting light for the CMOS image sensor, the second lens portion having at least one optical property that is different from a corresponding optical property of the first lens portion.

15. A self-illuminating CMOS imaging package comprising:
 a complementary metal oxide semiconductor (CMOS) chip including a CMOS image sensor for detecting light incident thereon from above;
 a die including a light-emitting diode (LED) configured to emit illumination propagating above and away from the image sensor; and
 a monolithic optical lens, optically coupled with the LED and the CMOS image sensor, and including: (i) a first lens portion directly above the LED, for projecting the illumination; and (ii) a second lens portion directly above the CMOS image sensor, for imaging light onto the CMOS image sensor, the second lens portion having at least one optical property differing from a corresponding optical property of the first lens portion.

16. The self-illuminating CMOS imaging package of claim 15, the monolithic optical lens being spaced apart from the LED and the CMOS image sensor, and further comprising an optical divider for isolating (a) a first optical pathway between the first lens portion and the LED from (b) a second optical pathway between the second lens portion and the CMOS image sensor.

17. The self-illuminating CMOS imaging package of claim 15, further comprising a cover glass for protecting the monolithic optical lens, the cover glass being positioned over (a) the first lens portion to transmit light emitted by the LED and projected by the first lens portion and (b) the second lens portion to transmit light through the second lens portion to the CMOS image sensor.

18. The self-illuminating CMOS imaging package of claim 15, further comprising at least one common electrical connection shared by the LED and the CMOS image sensor.

19. The microelectronics chip of claim 18, the at least one common electrical connection including a power lead and a ground lead.

\* \* \* \* \*